United States Patent [19]

Sutter et al.

[11] 4,328,593

[45] May 11, 1982

[54] UNIVERSAL JOINT PROSTHESIS WITH CAP

[75] Inventors: Franz Sutter, Niederdorf; Fritz Straumann, Waldenburg, both of Switzerland

[73] Assignee: Institut Straumann AG, Switzerland

[21] Appl. No.: 157,278

[22] Filed: Jun. 6, 1980

[30] Foreign Application Priority Data

Dec. 22, 1979 [CH] Switzerland .................. 11399/79

[51] Int. Cl.³ ............................................. A61F 1/24
[52] U.S. Cl. ........................................ 3/1.91; 3/1.913; 128/92 C; 128/92 CA
[58] Field of Search ..................... 3/1.9, 1.91, 1.912, 3/1.913; 128/92 C, 92 CA, 92 G

[56] References Cited

U.S. PATENT DOCUMENTS

| | | | |
|---|---|---|---|
| 2,537,070 | 1/1951 | Longfellow | 128/92 G |
| 4,007,494 | 2/1977 | Sauer | 3/1.9 |

FOREIGN PATENT DOCUMENTS

| | | |
|---|---|---|
| 837294 | 4/1952 | Fed. Rep. of Germany . |
| 876739 | 5/1953 | Fed. Rep. of Germany . |
| 2512407 | 9/1976 | Fed. Rep. of Germany . |
| 2634954 | 2/1978 | Fed. Rep. of Germany . |
| 2751537 | 5/1979 | Fed. Rep. of Germany ......... 3/1.92 |
| 2845231 | 5/1979 | Fed. Rep. of Germany ....... 3/1.912 |
| 59919 | 3/1954 | France ............................ 128/92 CA |
| 1095012 | 12/1954 | France ............................ 128/92 CA |
| 764600 | 12/1956 | United Kingdom ........... 128/92 CA |
| 1334584 | 10/1973 | United Kingdom ................. 3/1.912 |

OTHER PUBLICATIONS

"Histomorphological Investigation of Coxa Femoral Ends Following Double-Cup Arthroplasty According to Freeman" by M. D. Cserhati et al., Archives of Orthopaedic & Traumatic Surgery, 94, pp. 233–240, 1979.

Primary Examiner—Ronald L. Frinks
Attorney, Agent, or Firm—McGlew and Tuttle

[57] ABSTRACT

A prosthesis for forming the spherical part of a hip joint with a calotte-shaped cap is disclosed. The inner surface of the prosthesis is provided with grooves and ribs which are evenly distributed over the circumference of the inner surface and extend along planes which, in turn, extend through the rotational symmetry axis of the outer cap surface. A sleeve having jacket is provided with holes is rigidly secured at the inner end of the inner cap surface on the cap and projects partly out of the latter. The ribbing of the inner cap surface and the sleeve permit the prosthesis to be firmly and durably secured in an operation on the bone without cement.

14 Claims, 14 Drawing Figures

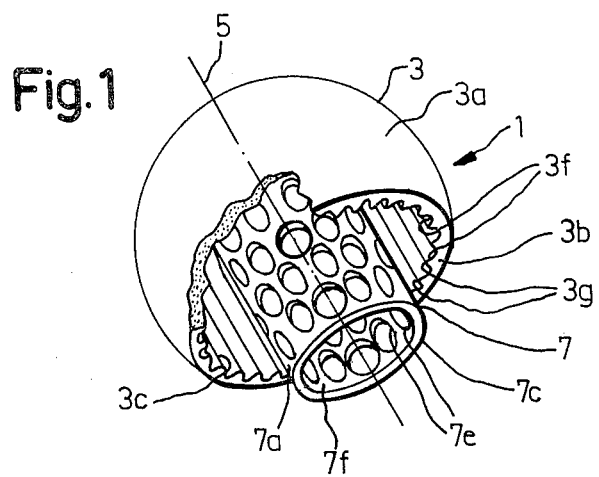
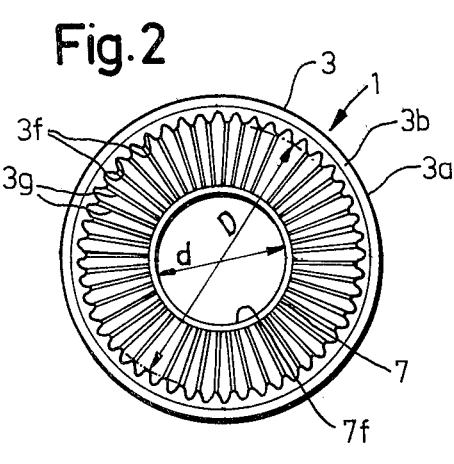
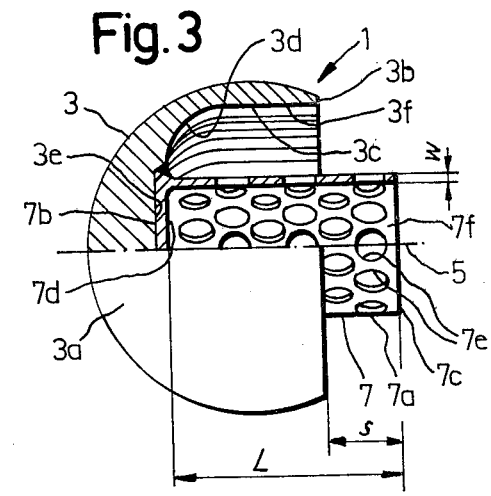

UNIVERSAL JOINT PROSTHESIS WITH CAP

BACKGROUND AND FIELD OF THE INVENTION

The invention relates to a universal joint prosthesis with a cap with a calotte-shaped outer surface.

A hip joint prosthesis disclosed in U.S. Pat. No. 3,808,606 has a metallic spherical part which is secured on a metallic thorn which can be anchored on a femur, that is, a thigh bone. A disadvantage of this known prosthesis is that the entire spherical part, as well as a part of the neck of the femur, must be removed. Furthermore, a deep hole must be drilled in the femur to anchor the thorn. Consequently, the femur is considerably weakened due to the large amount of healthy bone material that must be removed. Since foreign substances can lead to undesired reactions, the insertion of a prosthesis with so much metal is disadvantageous. Another disadvantage of this prosthesis is that the thorn has a much greater bending resistance than the bone part into which it protrudes. In the case of bending stresses, the thorn is therefore much stiffer than the bone and the areas of the bone in the proximity of the thorn are subject to extremely great stresses in bending.

Prostheses are already known which use a calotte-shaped cap as a substitute for the spherical part of the femur. The interior of the cap is bounded by a smooth cylinder surface, apart from an existing narrow and shallow ring slot, and at the inner end by a hemispherical or radial, likewise smooth surface. For the insertion of such a cap, the spherical part of the femur is cut off only to the extent that a pivot complementary to the interior of the cap remains.

In order to make sure that such a cap-shaped prosthesis fits firmly on the femur, it must be secured with a binder, the so-called cement. As it is known, for example, from the publication "Histomorphological Investigations of Coxa Femoral Ends Following Double Cup Arthroplasty According to Freeman", M.D. Cserhati, L. G. Oliveira, H. A. Jacob and A. Schreiber, Archives of Orthopaedic and Traumatic Surgery, 94, 233–240, 1979, this cement detaches in the course of time from the bony pivot and the cap becomes loose. Such prostheses, therefore, generally last only for a relatively short time.

The loosening of the prostheses is presumably caused, at least partly, by an unfavorable action of the cement on the spongiosa of the bone.

The axis of rotational symmetry of the bony pivot and of the cap in an upright standing patient with a prosthesis for a hip joint is inclined toward the vertical. On the other hand, the main stress is substantially vertical. Forces, therefore, appear naturally and quite frequently which form an angle with the rotational symmetry axis of the cap. Such forces are very likely another very important cause of the loosening of the cap because relatively great force components directed transverse to the rotational symmetry axis can then result, which extend with certain large relatively continuous sections of the inner cap surface more or less parallel or tangential to the inner cap surface. In these sections, there is only a minor transmission of forces between cap and femur, and the outer layers of the bony pivot are in addition stressed in shear. Furthermore, the cap and the bony pivot can then perform small movements relative to each other. If forces forming an angle with the rotational symmetry axis of the cup must thus be transmitted, this results in unfavorable and irregular stresses on the bony pivot.

SUMMARY OF THE INVENTION

An object of the invention is to provide a prosthesis for a universal joint with a calotte-shaped cap which can be secured on a bone firmly and durably without cement. The inventive prosthesis yields a possibly uniform distribution of the forces transmitted between the prosthesis and the bone, even in the transmission of forces with a component extending transverse to the rotational symmetry axis of the outer cap surface.

The term rotationally symmetrical smooth reference-osculating surface, as used herein, will be explained here more fully. The interior of the cap is hollow-cylindrical, apart from the ribs, a thread etc. The inner end face of the cap can be substantially hemispherical, conical or radial. In the latter two cases, either a sharp edge or a rounded transition can be provided between the cylindrical inner surface part and the conical or radial inner surface part. The phrase "reference-osculating surface" refers to the rotationally-symmetrical surface defined by a plane which adjoins the ribbed or threaded inner cap surface and which has an edge, at most, in the transition zone between the cylindrical inner surface part and the conical or radial inner end face but is otherwise smooth and steady. If a hollow-cylindrical sleeve is provided which is connected with the cap at the inner end face, the reference osculating surface must be so laid as if the sleeve did not exist.

Depressions and elevations formed in the inner cap surface increase the area of the latter with regard to the above mentioned rotationally-symmetrical smooth reference-osculating surface, so that the transmission of forces is improved. Since these depressions and elevations extend along lines which extend parallel or helically to the rotational symmetry axis of the outer cap surface, the depressions and elevations have another very important advantage, apart from the mere increase of the surface bearing on the bone. The axis of rotational symmetry of a cap secured on the femur of a patient is not vertical in an upright standing patient but inclined. The cap must, therefore, transmit forces which have a relatively large component directed transverse to the axis of rotational symmetry of the cap. When the portion of the lateral area of the inner cap surface is designed as a smooth cylindrical surface, pressure directed transverse to the axis of rotational symmetry of the cap are transmitted mainly in a narrow strip of the cylindrical inner surface part at the point of action of the forces from the cap to the femur. This results in relatively large local stresses on the cap and the femur at the transmission points.

If ribs, or corresponding elevations and depressions, are provided with flanks extending parallel to the rotational symmetry axis of the cap or helically, surfaces are obtained which are distributed over a relatively large portion of the circumference of the inner cap surface, and which can also transmit transverse forces directed transverse to the rotational symmetry axis distributed somewhat evenly over the entire circumference of the cap.

The depressions and elevations of the inner cap surface also permit the cap to be either pushed in axial direction over the bone or screwed on to the bone and to profile the bone. The prosthesis is thereby already given an initial hold during the insertion without the necessity of using bone cement.

The prosthesis according to the invention is particularly suitable for the formation of artificial hip joints but can also be adapted for the formation of other joints, like elbow-, shoulder- and finger joints.

Accordingly, it is an object of the invention to provide a universal joint prothesis which includes a calotte-shaped outer surface defined by a surface of revolution symmetrically disposed about a central longitudinal axis and terminating in a free edge and an inner surface extending from said free edge defining a concavity in which a bone or the like may be received. The inner surface has a plurality of spaced projections having depressions therebetween. The projections and depressions are successively arranged along lines extending from the free edge toward the innermost portion of the inner surface.

It is a further object of the invention to provide a universal joint prosthesis which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawings and descriptive matter in which there are illustrated a preferred embodiment of the invention.

BRIEF DESCRIPTION OF THE DRAWINGS

In the Drawings:

FIG. 1 shows a perspective view, partly broken away, of a prosthesis for a universal joint;

FIG. 2 shows a top view of the open side of the prosthesis of FIG. 1;

FIG. 3 shows a side elevation, partly in section, of the prosthesis of FIG. 1;

DETAILED DESCRIPTION

Figure 4:
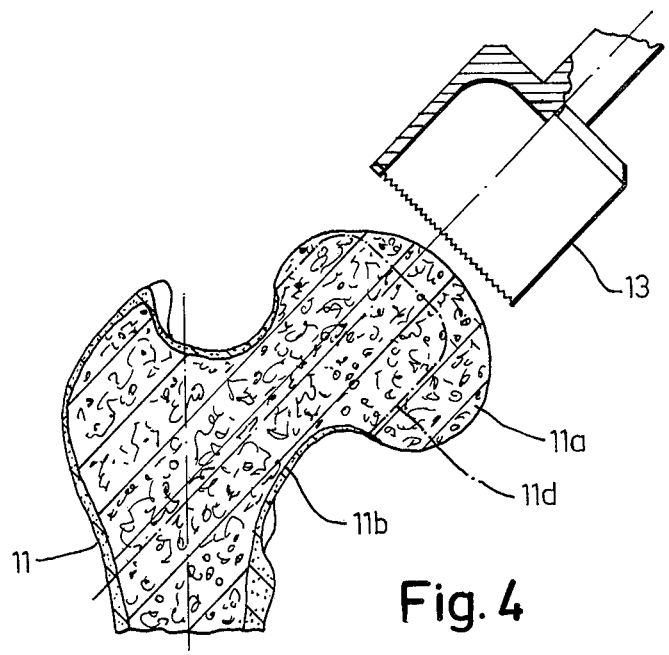
FIG. 4 shows a section through a femur and a milling cutter for cutting the outer surface of the spherical part thereof.

Prosthesis 1 represented in FIG. 1 to 3 serves as a substituted for the spherical part of a human hip joint. Prosthesis 1 includes a cap 3, whose outer surface 3a is formed in the shape of a calotte that is slightly larger than a hemisphere. The axis of rotational symmetry of the outer surface 3a is designated by reference numeral 5.

A sleeve 7 having a circular-cylindrical jacket 7a, arranged coaxially to the rotational symmetry axis 5, and is rigidly connected at the inner end of the interior of cap 3. The connection between cap 3 and sleeve 7 can be established, for example, by welding or by the production of a temperature difference and a shrink fit. Sleeve 7 is closed at the secured end by a bottom 7b having an inner bottom surface 7d. A free end 7c of sleeve 7 projects from the interior of the cap by an amount s, that is, beyond the plane extending from an edge 3b of cap 3. Sleeve 7 is open at its free end 7c, so that its circular-cylindrical interior 7f opens at the end 7c into the surrounding.

The interior of the cap is bound at the part adjoining cap edge 3b by an inner lateral area 3c, which is generally circular cylindrical, that is, it has a circular-cylindrical osculating surface, which extends coaxially in respect to the rotational symmetry axis 5 of the outer surface 3a. The generally cylindrical inner lateral area 3c is joined on the inside by a rounded transition area 3d tapering toward sleeve bottom 7d. The innermost part of the inner cap surface includes a depression 3e, which forms a step with the end of transition area 3d. The depth of this step is so dimensioned that the surface 7d, which extends radially to the rotational symmetry axis 5 and which faces the opened side of cap 3, is in the same plane as the inner edge of transition area 3d. If it is imagined that the cylindrical jacket 7a of sleeve 7 removed and surface 7d extended to the outside, this extension would pass over steadily into transition area 3d.

Areas 3c and 3d of the inner cap surface are provided with grooves 3f and ribs 3g in between, which are distributed evenly over the circumference of the inner cap surface. At least 20, and for example about 30 grooves and ribs are provided. Each groove 3f and rib 3g extends along a plane extending through the axis of the rotational symmetry from the edge of cap to the transitional area 3d. As it can be seen particularly from FIG. 7, grooves 3f are wider than ribs 3g. All transitions between grooves 3f and ribs 3g are continuously rounded. The depth t of the grooves 3f is in the zone of the area 3c at least 2.5%, and namely slightly more than 5% of diameter D of a circular-cylindrical osculating surface 9 which is rotationally symmetrical to axis 5 and which hugs the zenithal lines of ribs 3b. In the range of transition area 3d the groove depth diminishes, so that the grooves and ribs terminate substantially at the inner edge of transition area 3d.

The inside diameter d of sleeve 7 is at least 25%, and preferably at least 35% of diameter D of osculating surface 9. On the other hand, the inside sleeve diameter d is at most 75%, and preferably at most 60% of diameter D of osculating surface 9. In a hip joint prosthesis, diameter D is, for example, 35 to 42 mm and diameter d about 10 to 25 mm.

The wall thickness w of sleeve jacket 7a, measured in radial direction, is at least 1%, and preferably 3%, as well as at most 30%, and preferably at most 18%, of the inside sleeve diameter d. Preferably the wall thickness w is between 4 and 8% of the inner sleeve diameter d. With the diameters provided for hip joint prostheses, the wall thickness is at least 0.3 mm and preferably at least 0.5 mm. Furthermore, the wall thickness w is at most 3 mm, and preferably at most 2.5 mm. The inside sleeve diameter d is at least 10%, and preferably at least 30%, of the length L of sleeve interior 7f. In a prosthesis for the formation of a hip joint, the length L should preferably be at most 50% greater than diameter D, and preferably approximately equal to the latter. Furthermore the distance s is at most 50%, and preferably at most 40% of length L. In prostheses for other joints, particularly prostheses for elbow joints, the ratios L/D and s/L can be higher.

Jacket 7a of sleeve 7 is provided with macroscopic holes 7e extending therethrough and evenly distributed over its circumference and its length, namely bores. The diameter of these holes 7e can be 3% to 60%, and preferably about 15 to 30% of the inside diameter d of sleeve jacket 7a. In a hip joint prosthesis, the holes 7e have preferably a diameter of 3 to 6 mm. The dimension and intervals of holes 7e are so adapted to each other that the part of the inner surface of sleeve jacket 7a occupied by holes 7e is at least 30%, and at most 70% of the entire inner surface of the jacket sleeve.

If grooves 3f, ribs 3g, and the jacket 7a of sleeve 7 were not provided, cap 3 could bear on the bone only with its reference osculating surface. This reference osculating surface is, in the present case, the surface rotationally symmetrical to axis 5, which hugs the zenithal lines of ribs 3g and coincides at the inner edge of the sleeve interior with the radial surface 7d of the sleeve bottom. (depression 3e would not be provided in the absence of the sleeve.) In the prosthesis 1, the inner surface of cap 3 is increased in the range of its sections 3c and 3d by grooves 3f and ribs 3g. Furthermore, sleeve 7 can bear on the bone with the inner and outer surface of its jacket 7a, as well as the bottom surface 7d. The ribbing of a part of the inner cap surface proper and the sleeve 7 thus yield a considerable increase in the surface that can bear on the femur after the insertion of prosthesis 1. Due to the ribbing of the inner cap surface and sleeve 7, the surface that can bear on the femur with the use of a prosthesis is increased to a value which is at least double or triple the size of the reference-osculating surface.

Cap 3 and sleeve 7 are made of metal, for example, of stainless steel or titanium. The inner surface of cap 3 and the inner and outer surface of sleeve 7 can be covered with a porous, sprayed-on titanium coating to increase the surface roughness or it can be treated in any other way. The roughening, however, is so applied that the depths and heights of the depressions and elevations formed by them are at most 10% of depth t of grooves 3f. The profiling of the inner cap surface resulting from grooves 3f and ribs 3g is thus substantially maintained despite the titanium coating and other surface roughening.

Figure 5:
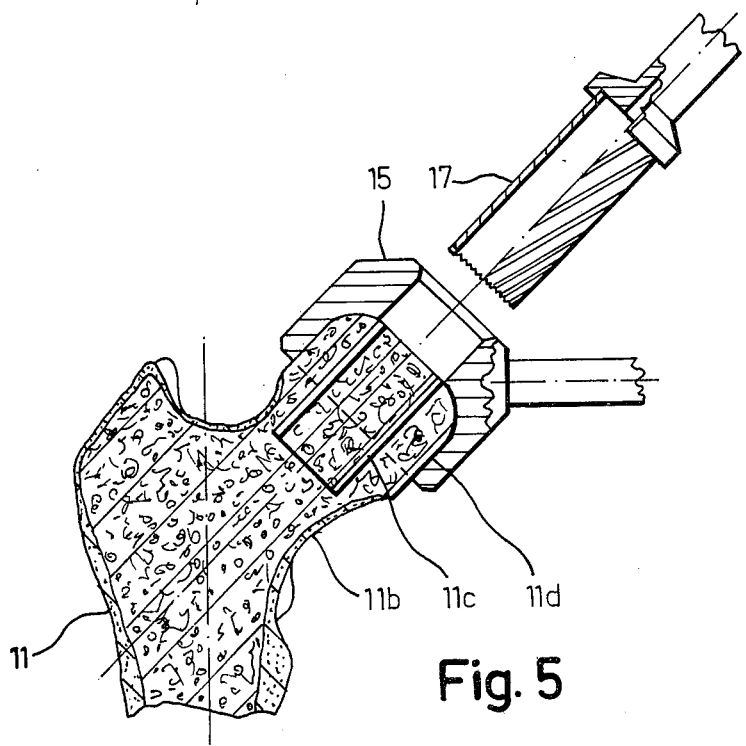
FIG. 5 shows a section through a femur and the tools for cutting a ring slot to receive the sleeve of the prosthesis.
Figure 6:
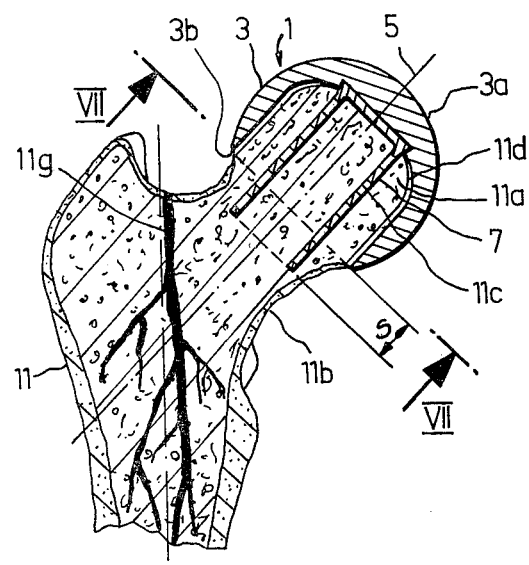
FIG. 6 shows a femur with an attached prosthesis directly after the attachment.

In practice, the prosthesis is secured on a femur as follows. As shown in FIG. 4, a femur 11 has a head 11a, which is connected to the rest of the femur by a neck 11b. In an operation, head 11a of the femur 11 is first exposed. Then the outer layer of head 11a is cut off by means of a milling cutter 13, so that only a pivot 11d with the outlines shown in FIG. 4, in dot-dashed lines, remains on head 11a. On this pivot is then attached a gauge 15, as shown in FIG. 5, and a hollow slot 11c is cut into pivot 11d with a hollow end milling cutter 17 guided by gauge 15. Then, prosthesis 1 is engaged on the femur pivot in the manner shown in FIG. 6, so that the inner surface of cap 3 applies against pivot 11d and sleeve 7 extends into slot 11c.

Figure 7:
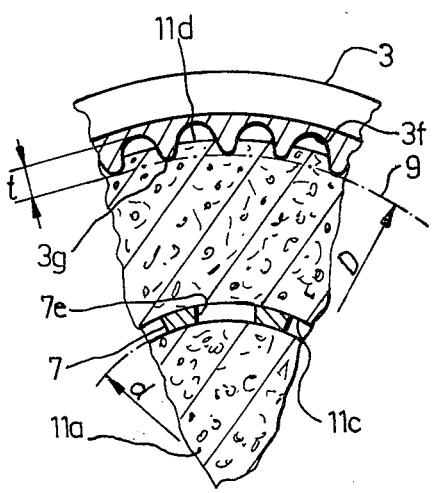
FIG. 7 shows an enlarged section taken along line VII—VII of FIG. 6.

The surface contour of pivot 11d formed in the cutting of the outer layer of head 11a is substantially complementary to the inner surface of cap 3. As is best shown in FIG. 7, the outside diameter of femur pivot 11d is made larger, in the vicinity of inner cap surface 3c by groove depth t, than the diameter of reference-osculating surface 9. Ribs 3g must therefore be pressed into the bone material when prosthesis 1 is attached in femur pivot 11d in the direction of rotational symmetry axis 5. The cylindrical part of the boundary surface femur-pivot 11d is profiled, so that the femur pivot extends down to half the depth of grooves 3f and the prosthesis immediately sits relatively firmly on the femur. In addition, the width of the circular ring slot 11c is so dimensioned that sleeve 7 fits tightly on it or must be pressed into the latter. This permits the prosthesis to be secured on the femur without cement.

Figure 8:
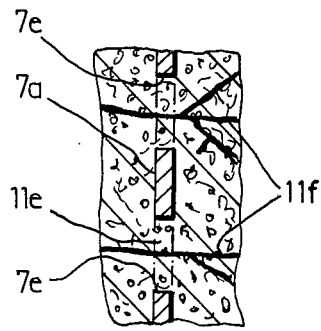
FIG. 8 shows a longitudinal section through a part of the sleeve jacket, after the bone material has grown through holes provided in the sleeve jacket.

In the course of time, the femur can grow into grooves 3f so far that they are filled completely with bone material. The dimensions of the sleeve interior 7f of the sleeve and the holes 7e ensure that the bone material and the blood vessels 11f in the vicinity of femur pivot 11d also grow through holes 7e in sleeve jacket 7a, as shown in FIG. 8. The bone material forms then bridges 11e, which penetrate through holes 7e. Each bridge 11e is connected on the inside and outside of sleeve jacket 7a with sections of the bone material, which then form so-to-speak adjoining flanges, and with the latter a double T. Furthermore, the bone material can grow into the pores of the sprayed-on titanium coating or the roughening formed in any other way. The prosthesis is therefore anchored very firmly and durably in the femur. Sleeve 7, whose wall is thin compared to its diameter, shows only a small additional loss of natural bone material. The spongiosa lamellae can also grow along the main stress lines, that is, the lines of greatest stress, both within the sleeve and in the range of the bony pivot surrounding the latter and through the through-holes 7e, similar as in a bone without prosthesis. The result is a similar flux of forces as in a natural joint, which likewise contributed to the stability of the bone-prosthesis connection.

Figure 9:
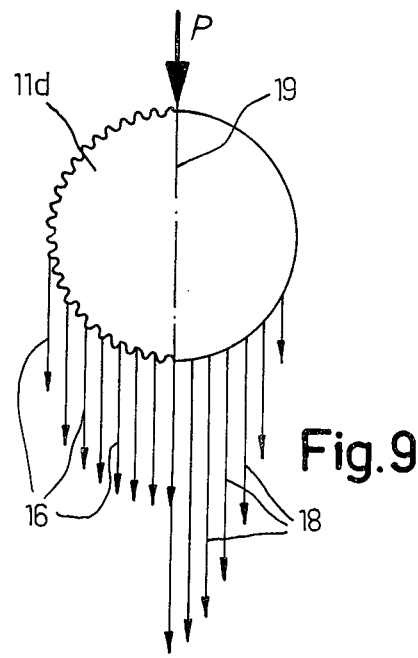
FIG. 9 shows a diagrammatic illustration of the transmission of forces at the circumferential surface of the bone part protruding into the cap, showing in the left portion of the figure for comparison the distribution of forces for a prosthesis with a ribbed inner cap surface and in the right portion of the figure the distribution of forces for a prosthesis with a smooth-cylindrical inner cap surface.

Reference may now be made to FIG. 9 to determine how a force P, directed transversely to the rotational symmetry axis 5, is transmitted from femur pivot 11d to cap 3 of prosthesis 1, when the femur has grown in the above-described manner into grooves 3d. Force P is assumed to be directed parallel to a straight line 19, which intersects rotational symmetry axis 5 at a right angle. The left half of FIG. 8 schematically shows the contour of femur pivot 11d, which has formed grooves complementary to grooves 3f of cap 3. The flanks of these grooves form surfaces, even at the point of the periphery farthest away from straight line 19, which are not parallel to the direction of force P, but form an angle between 45 and 135 degrees with that direction. This ensures that forces will be transmitted from the femur to the cap and vice versa even at the peripheral points farthest away from straight line 19. In the transmission of force P, the latter is therefore divided into partial forces whose size and local distribution is indicated qualitatively by arrows 16. Force P to be transmitted is evenly distributed over a large portion of the circumference of cap 3 and of femur pivot 11d respectively. Furthermore, sleeve 7 also naturally contributes to the transmission of the force. This results in a relatively uniform distribution of the forces and stresses of the bone material.

If the inner cap surface and the femur pivot surface bearing on it were smooth cylinder-surfaces, however, this would result in partial forces represented qualitatively in the right half of FIG. 9 by arrows 18. The peripheral areas of the cap and of the femur pivot farthest away from straight line 19 would then be practically useless for the transmission of force P.

Since sleeve 7 protrudes deeper in the femur by the amount s than the latter is embraced by the cap, the risk that the femur will be sheared off at the edge 3b of cap 3 with large forces acting transverse to the rotational symmetry axis 5 is very small. The inner length L of the sleeve and the distance s are dimensioned so that sleeve 7 does not extend up the main vein strand designated with 11g in FIG. 6, which extends substantially along the center axis of the femur shaft, and which is so important for the blood supply of the bone.

If forces act at a certain point of prosthesis 1 with a component directed transverse to the rotational symmetry axis 5, bending stresses will also appear. In the theory of elasticity of a body, the so-called bending resistance is used to characterize the bending behavior of a body, which is equal to the product area inertia I times modulus of elasticity E, and therefore depends both on the geometric dimensions of the respective body and on its material, namely on its modulus of elasticity. The bending resistance of the bone can differ greatly for different patients. But by suitable dimensioning of sleeve 7, the bending resistances of sleeve 7 and of the bone can be so adapted to each other that they are of comparable orders of magnitude and that both the femur and the sleeve 7 are slightly bent under bending stresses. This has likewise a favorable effect on the transmission of forces and the durability of the anchorage of the prosthesis.

Figure 10:
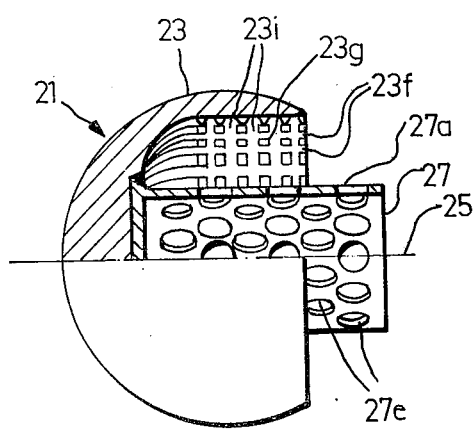
FIG. 10 shows an alternate embodiment of a prosthesis, similar to FIG. 3, having an inner cap surface which is provided with grooves extending parallel to the axis of rotational symmetry and with annular grooves.

In order to prevent great shearing forces at the edge of the free, open end 7c of sleeve 7 in bending stresses, it is particularly advantageous if at least the free end section of sleeve 7 projecting from the interior of the cap has a bending resistance which is similar to the bone, or not too much greater than that of the bone. For this section of the sleeve, however, that is inside cap 3, a somewhat greater bending resistance is permissible, and even advantageous. Sleeve 7 can, therefore, also be designed so that its free end section has a lower bending resistance than the end section secured on the cap and than that of its central section. The bending resistance along the sleeve can either very in bounds or steadily. In order to realize this variance in bending resistance along the sleeve, the ratio of lateral area occupied by through-holes 7e to the unperforated lateral area in the range of the free sleeve end 7c can be slightly increased. Another possibility would be to make the wall thickness w at the free end 7c of sleeve 7 somewhat smaller than at the other end and in the central part of the sleeve. The inner or outer surface or both of sleeve jacket 7a is naturally no longer strictly cylindrical in the latter case, but the deviation from the cylinder form is not very great. It should be noted that the bending resistance can also be varied naturally in the other sleeves described below in connection with FIGS. 10 to 13 in a similar manner along the longitudinal axis of the sleeve. Prosthesis 21 represented in FIG. 10 has a cap 23 and a sleeve 27. The inner surface of cap 23 is provided with grooves 23f which extend along planes through the rotational symmetry axis 25 and which correspond to grooves 3f. The inner surface, however, is also provided with additional ring-shaped grooves 23i, which can have substantially the same depth as grooves 23f. Between the intersecting grooves, there are than a plurality of cams 23g projecting into the interior of cap 23. Jacket 27a of sleeve 27 is provided with holes 27e, like jacket 7a.

Figure 11:
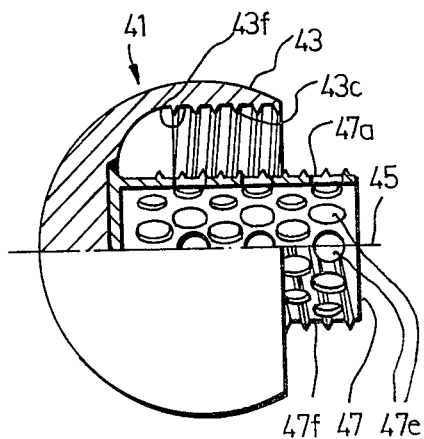
FIG. 11 shows still another alternate embodiment of a prosthesis, corresponding to FIG. 3, whose inner cap surface and outer sleeve surface are provided with a thread.

Prosthesis 41 represented in FIG. 11 has a cap 43 whose substantially cylindrical inner surface part 43c is coaxial to the rotational symmetry axis 45 of the outer cap surface and which has a groove 43f extending along a helix and forming a continuous thread. The outer surface of jacket 47a of sleeve 47 is likewise provided with a groove 47f extending along a helix and forming a thread. The two threads have the same direction of rotation and the same pitch, so that the prosthesis can be secured on the femur. Sleeve jacket 47a is also provided with holes 47e corresponding to holes 7e. In the embodiment represented in FIG. 11, the inner surface of the cap could be provided with grooves, in addition to grooves 43f, which extend along planes through axis 45. Just as in the case of cap 23, we would then have a plurality of cams which form fragments of a thread. Furthermore, the threads could also be multiple threads.

Prosthesis 41 can be screwed in an operation on the pre-cut femur pivot by rotating it about the rotational symmetry axis 45. If the diameters of the outer surface of the femur pivot and of the ring slot cut into the latter are fixed, the threads of the prosthesis can cut into the bone material when the prosthesis is screwed on. Prosthesis 41, just like the previously described model, fits immediately firmly on the bone after it has been inserted.

Figure 12:
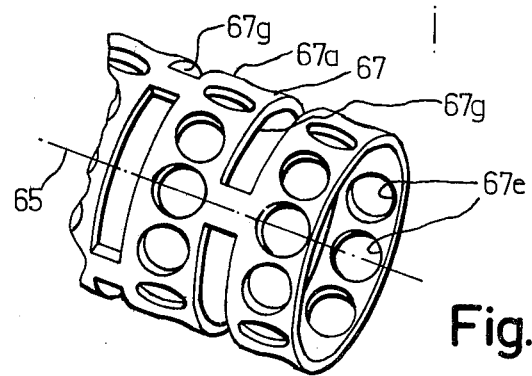
FIG. 12 shows a part of a sleeve with a jacket having both round and slotted holes.

FIG. 12 shows a variant of a sleeve 67, of which only a part of jacket 67a is represented, and which like sleeve 7, is rigidly connected at one end with a cap (not shown) and is open at the other end. Sleeve jacket 67a is provided with two types of holes extending therethrough namely with circular bores 67e and with slots 67g. Ring-shaped areas which contain either bores or slots follow each other alternately in the direction of rotational symmetry axis 65. Slots 67g have an elongated form, their longer edges extending along circular arcs.

Figure 13:
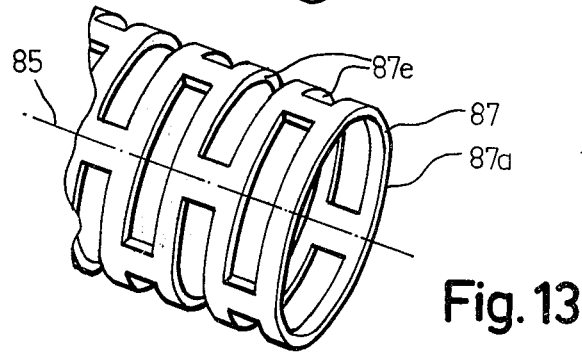
FIG. 13 shows a part of a sleeve with slotted holes.

FIG. 13 shows a part of a jacket 87a of a sleeve 87, which is rigidly connected at one end with a cap (not shown) and open at the other end. Jacket 87a is provided with through-holes, namely oblong slots 87e, whose longer edges extend along circular arcs about rotational symmetry axis 85. Ring-shaped areas of jacket 87a containing each three slots distributed over the circumference are provided in succession.

In prostheses 1, 21 and 41, the inner end of the inner cap surface is formed by a plane, radial surface which is connected with the cylindrical part of the inner surface by a rounded transition area. An edge could also be provided between the radial, or possible conical, inner end face and the cylindrical inner surface of the cap.

Figure 14:
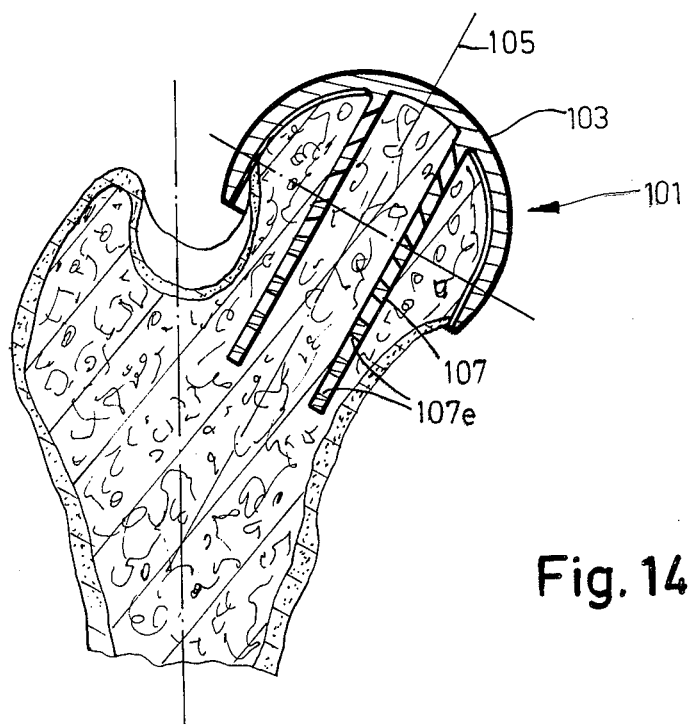
FIG. 14 shows a section through femur, corresponding to FIG. 6, with another variant of a prosthesis.

As it is the case in prosthesis 101 represented in FIG. 14, cap 103 can have also an inner surface, or more accurately an inner enveloping surface whose inner end, apart from sleeve 107, is formed by a hemispherical surface, which passes over steadily into the cylindrical part of the inner surface. The part of the inner surface outside sleeve 107 is provided with ribs and grooves distributed over the circumference, which extend along planes, which in turn extend through the rotational symmetry axis 105. Sleeve 107 is in this embodiment integral with cap 103. The sleeve is provided with through holes 107e distributed over its lateral area. The holes provided next to the inner sleeve end are inclined toward axis 105 for manufacturing reasons.

It should be noted that the cap and sleeve forms of the above described embodiments can be combined with each other in various ways.

In all the embodiments described above, the inner cap surface of the prosthesis has several successive depressions and elevations in a section laid transverse to the rotational symmetry axis of the outer cap surface or in a section laid parallel to the said axis or both. The inner cap surface, which can bear on the femur after the prosthesis has been inserted, can therefore be at least 50%, and even more than 100% larger than the respective reference-osculating surface. If we add the inner-and outer surface of the sleeve jacket, the surface that can bear on the femur can even be at least 200% larger than the reference osculating surface.

The represented prostheses are intended to be secured on a femur to form the spherical part of an artificial hip joint. But the prostheses can also be so dimensioned that they can be used as a spherical part for an elbow-, shoulder- or finger joint.

While specific embodiments of the invention have been shown and described in detail to illustrate the application of the principles of the invention, it will be understood that the invention may be embodied otherwise without departing from such principles.

What is claimed is:

1. A universal joint prosthesis for engaging the head portion of a bone end while retaining the major portion thereof, comprising a cap having a calotte-shaped outer surface terminating in a free edge and an inner surface having a reference osculating surface which is symmetrical about a central longitudinal axis, extending from said free edge defining a concavity in which a bone or the like may be received, the concavity being sufficiently large to contain a major portion of the cancellous bone end of the joint, said inner surface having a plurality of spaced projections, said projections being spaced to define depressions therebetween, said projections and depressions being successively arranged along lines extending from said free edge toward the innermost portion of said inner surface, said lines extending along planes laying in said longitudinal axis, an open ended sleeve attached to said inner surface and arranged coaxially to said axis and extending at least partly beyond the free edge of said concavity and rigidly connected to said cap, said sleeve including a plurality of macroscopic holes extending therethrough, said concavity as well as said projections and depressions extending from said free edge toward a depth where said inner surface converges toward said axis in a direction away from said free edge, wherein said projections and depressions increase the inner cap surface which can bear on a bone after the prosthesis has been inserted at least 50% with respect to the reference osculating surface that would limit the concavity if the projections and depressions and the sleeve are absent.

2. A prosthesis according to claim 1 wherein said inner surface of the cap includes at least twenty depressions distributed over the inner periphery of the cap which extend along planes extending through the longitudinal axis.

3. A prosthesis according to claim 2 wherein said inner surface of the cap further comprises grooves which extend at a right angle to said longitudinal axis.

4. A prosthesis according to claim 1 wherein said inner surface of the cap comprises at least one groove extending along a helix.

5. A prosthesis according to claim 1 wherein said inner surface includes a circular-cylindrical osculating surface having at least part of said depressions.

6. A prosthesis according to claim 5, wherein each of said depressions has a depth in the said inner surface at least 2.5 percent of the diameter of the circular-cylindrical osculating surface.

7. A prosthesis according to claim 5, wherein said inner surface includes a rounded transition area (3d) joining said cylindrical surface and tapering toward said axis (5) in the direction away from said free edge and wherein said projections and depressions extend over at least a part of said rounded transition area.

8. A prosthesis according to claim 1, wherein the said projections and depressions increase the inner cap surface by at least 100% with reference to said osculating surface.

9. A prosthesis according to claim 1, wherein the sum of the inner surface of the cap and the surfaces of said sleeve that can bear on a bone is at least 200% greater than said osculating surface.

10. A prosthesis according to claim 1 wherein the projections and depressions as well as transitions therebetween are, in a cross-section taken across said axis free of sharp corners.

11. A prosthesis according to claim 1 wherein a free end of said sleeve projects beyond said cavity by an amount(s) that is at most 50% of the total length(L) of an interior of said sleeve.

12. A prosthesis according to claim 1, wherein a free end of said sleeve projects beyond said cavity by an amount (s) that is at most 40% of a total length (L) of the interior of said sleeve.

13. A method of securing a prosthesis according to claim 1, to a joint head of a bone comprising:
cutting off an outer layer portion of the joint head to form a pivot having a shape substantially corresponding to the cap concavity and having a diameter slightly larger than a diameter of the reference osculating surface;
cutting a cylindrical slot into the pivot having a shape substantially similar to that of said sleeve; and
pressing the prosthesis onto the pivot with the cap concavity firmly receiving the pivot and the sleeve moving into the cylindrical slot.

14. A method according to claim 13, wherein the pivot and slot have dimensions so that, upon pressing the prosthesis onto and into the pivot and slot respectively, an immediate firm cement free mounting is established between bone of the pivot and slot and the prosthesis.